United States Patent [19]

Watson et al.

[11] Patent Number: 5,360,929
[45] Date of Patent: Nov. 1, 1994

[54] PROCESS FOR THE PRODUCTION OF CARBOXYLIC ACID ANHYDRIDES

[75] Inventors: Derrick J. Watson, East Yorkshire; Bruce L. Williams; John G. Sunley, both of North Humberside; Robert J. Watt, Middlesex, all of England

[73] Assignee: BP Chemicals Limited, London, England

[21] Appl. No.: 196,284

[22] Filed: Feb. 10, 1994

[30] Foreign Application Priority Data

Feb. 25, 1993 [GB] United Kingdom ............... 9303770

[51] Int. Cl.$^5$ .................. C07C 51/12; C07C 53/12
[52] U.S. Cl. ................... 562/891; 562/890
[58] Field of Search ................. 562/891, 890

[56] References Cited

U.S. PATENT DOCUMENTS

| | | | |
|---|---|---|---|
| 4,328,125 | 5/1982 | Drago | 252/426 |
| 4,374,070 | 2/1983 | Larkins | 562/891 |
| 4,534,912 | 8/1985 | Cook | 562/891 |
| 4,559,183 | 12/1985 | Hewlett | 562/891 |
| 4,874,558 | 10/1989 | Fife | 562/894 |
| 5,155,261 | 10/1992 | Marston | 562/519 |
| 5,189,203 | 2/1993 | Hansen et al. | 562/890 |
| 5,220,060 | 6/1993 | Lapporte et al. | 562/891 |
| 5,298,586 | 3/1994 | Beevor et al. | 562/891 |

FOREIGN PATENT DOCUMENTS

| | | |
|---|---|---|
| 1188321 | 4/1985 | Canada . |
| 98689 | 6/1982 | European Pat. Off. . |
| 87869 | 9/1983 | European Pat. Off. . |
| 0277824 | 8/1988 | European Pat. Off. . |
| 3235051 | 3/1984 | Germany . |
| 1149748 | 6/1989 | Japan . |
| 2140004 | 11/1984 | United Kingdom . |

OTHER PUBLICATIONS

Chen, Yuying et al, Acta Chimica Sinica, 1990, 48, 121-126.
Chen, Yuying et al, J. Molecular Catalysis, vol. 2, No. 8, Sep. 1988.
Yuan Guoqing et al, Chinese Journal of Polymer Science, vol. 7, No. 3, 1989, pp. 220-224. "A Novel Copolymer-Bound CIS-Dicarbonylrhodium Complex for the Carbonylation of Methanol to Acetic Acid and Acetic Anhydride".
Chen Yuying, et al, Chinese Journal of Polymer Science, vol. 7, No. 3, 1989, pp. 226-231, "Kinetic Study of Carbonylation of Methanol to Acetic Acid and Acetic Anhydride Over a Novel Copolymer-Bound CIS-Dicarbonylrhodium Complex".

Primary Examiner—Paul J. Killos
Attorney, Agent, or Firm—Brooks Haidt Haffner & Delahunty

[57] ABSTRACT

A process for the production of a carboxylic acid anhydride comprises contacting a reaction composition comprising a carboxylic acid ester, a hydrocarbyl halide and/or a hydrocarbyl ether reactant and a hydrocarbyl halide promoter with carbon monoxide in the presence of a catalyst comprising an insoluble polymer support having pendant quaternised N-base or alkylated N-oxide pyridine groups supporting a rhodium species in which process the rhodium species is prevented from leaching from the polymer support by maintaining throughout the process a finite concentration of carboxylic acid anhydride in the reaction composition.

10 Claims, No Drawings

PROCESS FOR THE PRODUCTION OF CARBOXYLIC ACID ANHYDRIDES

This invention relates to a process for the production of carboxylic acid anhydrides and in particular to a process for the production of carboxylic acid anhydrides in the presence of a carbonylation catalyst comprising a polymer supported rhodium species.

Carbonylation processes are known in which small organic molecules such as alkenes, alkynes, alcohols, esters, hydrocarbyl halides or hydrocarbyl ethers are reacted with carbon monoxide in the liquid phase and in the presence of a transition metal catalyst, for example rhodium. When esters, hydrocarbyl halides or hydrocarbyl ethers are used as reactants carboxylic acid anhydrides can be produced. It is usual in such processes to use a homogeneous transition metal catalyst.

U.S. Pat. No. 4,328,125 describes heterogeneous anionic transition metal catalysts containing a catalytically effective amount of an anionic species having the formula $M_n(CO)_m(X)_p{}^{1-}$, said anionic species being ionically bound to an insoluble crosslinked anion exchange resin containing a bound quaternary ammonium cation. Such catalysts are said to effect carbonylation and hydroformylation reactions and are said to be prepared by treating a resin containing a polymeric quaternary ammonium salt with a neutral transition metal carbonyl compound. Suitable resins are said to include polyvinyl pyridines and polystyrene bound pyridineso The Examples given in U.S. Pat. No. 4,328,125 all relate to rhodium supported catalysts. All of the examples of carbonylation reactions in U.S. Pat. No. 4,328,125 take place in the presence of water and/or methanol to produce acetic acid. Leaching of rhodium is observed at elevated temperature during the carbonylation of methanol in Examples 12 and 13. The carbonylation reaction conditions reported in U.S. Pat. No. 4,328,125 are 54–162 psi and up to 130° C.

U.S. Pat. No. 5,155,261 describes a process for the carbonylation of methanol to acetic acid which uses a heterogeneous catalyst comprising an insoluble polymer having pendant free base, N-oxide or quaternised pyridine groups or a combination thereof supporting a rhodium species loaded to less than about 10 weight percent (expressed as metal) of the polymer component. Most preferred catalysts are said to be porous crosslinked 4 or 2-vinylpyridine copolymers in the free base or N-oxide form which have been quaternised either preformed or in situ with an alkyl halide such as methyl iodide and loaded at about 2 weight percent by reaction with a rhodium salt such as rhodium chloride trihydrate in an initial or generation run.

Whilst U.S. Pat. No. 5,155,261 states at Column 9, lines 31–32 that the "Applicants saw no leaching of rhodium metal in their experiments" it has now been found, contrary to the description of U.S. Pat. No. 5,155,261, that rhodium is leached from a polymer support under typical carbonylation conditions of high pressure and temperature in the presence of an aqueous liquid phase. Such leaching of rhodium may present difficulties, for example requiring recovery of the rhodium if the process is to be operated continuously.

The technical problem to be solved therefore, is to provide a carbonylation process in which the rhodium species of the carbonylation catalyst is not leached from the polymer support during the carbonylation reaction.

Accordingly, the present invention provides a process for the production of a carboxylic acid anhydride which process comprises contacting a reaction composition comprising a carboxylic acid ester, a hydrocarbyl halide and/or a hydrocarbyl ether reactant and a hydrocarbyl halide promoter with carbon monoxide in the presence of a catalyst comprising an insoluble polymer support having pendant quaternised N-base or alkylated N-oxide pyridine groups supporting a rhodium species, in which process there is maintained throughout the process a finite concentration of carboxylic acid anhydride in the reaction composition.

By using a reaction composition in which there is maintained a finite concentration of carboxylic acid anhydride, the reaction composition is maintained substantially anhydrous and substantially no water and/or alcohol will be present in the reaction composition. This maintains the rhodium species bound to the polymer support.

By finite concentration of carboxylic acid anhydride is meant at least 0.1% by weight. By substantially no water and/or alcohol is meant less than 0.1% by weight of either water or alcohol. Controlled amounts of water and/or alcohol may be introduced to the reaction composition to co-produce carboxylic acid in the process, provided that the reaction composition is maintained substantially free of water and/or alcohol.

The reaction of the present invention may be performed in the vapour or liquid phase.

The supported rhodium species is any rhodium containing compound which is capable of binding to the pendant quaternised or alkylated pyridine groups of the insoluble polymer support to give an active carbonylation catalyst.

The catalyst may suitably be prepared by reacting a polymer having pendant N-base or N-oxide pyridine groups in the free base form with a rhodium containing compound and a hydrocarbyl halide under typical carbonylation conditions either in situ or in an initial or generation run. Alternatively, such a free base polymer may first be reacted with a hydrocarbyl halide before being reacted with a rhodium containing compound under typical carbonylation conditions either in situ or in an initial or generation run. The hydrocarbyl group of the hydrocarbyl halide used to prepare the catalyst is preferably the same as the hydrocarbyl group of the reactant and preferably the hydrocarbyl halide is an alkyl iodide for example methyl iodide.

Examples of suitable rhodium containing compounds to be used in the preparation of the catalyst are $RhCl_3$, $[\{Rh(CO)_2Cl\}_2]$, $RhCl_3$ hydrate, $RhBr_3$ hydrate, $RhI_3$, $Rh(OH)_3$, $Rh_2O_3$ and rhodium acetates. The rhodium species on the support is present typically at 500 ppm to less than about 4% rhodium (as metal) by weight of the catalyst, preferably 0.05 to 0.4% rhodium by weight.

The polymer support is a polymer which is insoluble in the reaction composition and is stable under the carbonylation reaction conditions. Preferably, the polymer support is a porous cross-linked 4- or 2-vinyl pyridine copolymer in the free base or N-oxide form which has been respectively prequaternised or prealkylated or is respectively quaternised or alkylated in situ with a hydrocarbyl halide such as an alkyl halide, for example, methyl iodide.

More preferably, the polymer support is prepared from a porous cross-linked poly (4- and 2-vinylpyridine) copolymer such as those commercially available under the Reillex TM family of trademarks. In these Reillex TM copolymers, pyridine rings are attached directly at their 4- or 2- positions to the polymer backbone which is in turn cross-linked with some percentage of divinyl benzene being present. Reillex TM 425, for example, is a preferred polymer being a 25% cross-linked copolymer of 4-vinyl pyridine and a commercially available divinylbenzene exhibiting a convenient insoluble bead form, high porosity, good thermal stability, and high concentration of metal binding sites. Reillex TM 425 is typically available in bead sizes of approximately 18–50 mesh. The temperature stability for extended use of Reillex TM 425 polymer is about 260° C. which is particularly practical for commercial carbonylation of esters, hydrocarbyl halides and hydrocarbyl ethers to give carboxylic acid anhydrides at temperatures up to 250° C., preferably to 200° C.

Other preferred polymers include, for example, other crosslinked poly (4- and 2- vinylpyridine) copolymers such as those commercially available under the Reillex TM 402 and 225 trademarks. Of these, Reillex TM 225 is a 25% cross-linked copolymer of 2-vinylpyridine and a commercially available divinylbenzene. Reillex TM 402 is a 2% cross-linked copolymer of 4-vinylpyridine and a commercially available divinylbenzene. In other relevant respects, Reillex TM 225 is similar in its performance to the Reillex TM 425 described above. Reillex TM 402 is a granular powder, in contrast to the bead forms of Reillex TM 225 and 425, with a particle size of about 60 mesh and a slightly lower, but still acceptable, maximum temperature for extended use of about 225° C.

In addition to Reillex TM polymers, other polymers having pyridine, or pyridyl groups are suitable for preparing the catalyst of the present invention. These include polymers such as KEX TM-316 polymeric amine resin. Crosslinked polymers containing vinylpyridines may be prepared by reaction of the appropriate vinylpyridine, divinyl benzene and styrene in toluene and in the presence of benzoyl peroxide and an aqueous solution of hydrocellulose, sodium chloride and sodium hydride. This preparation is described in U.S. Pat. No. 5,255,261. The polymers used in the present invention may have in excess of about 50% pyridine levels.

In the carbonylation process of the present invention the ester reactant is an ester of an alcohol and a carboxylic acid. Preferably, the ester reactant is an ester of a $C_1$–$C_6$ carboxylic acid and a $C_1$–$C_6$ monofunctional aliphatic alcohol. A mixture of ester reactants may be used. Most preferably the ester reactant is an ester of a carboxylic acid and methanol, ethanol or propanol. A particularly preferred ester reactant is methyl acetate. The halide reactant is any hydrocarbyl halide, preferably a $C_1$–$C_6$ hydrocarbyl halide. Preferably, the halide reactant is an iodide or bromide. More preferably the halide is an alkyl iodide, most preferably methyl iodide, ethyl iodide or propyl iodide. A mixture of hydrocarbyl halides may be used. The ether reactant is any hydrocarbyl ether, preferably a $C_1$–$C_6$ hydrocarbyl ether. Preferably, the ether reactant is a dialkyl ether, most preferably dimethyl ether, diethyl ether or dipropyl ether. A mixture of ethers may be used. A particularly preferred reactant is dimethyl ether. A mixture of ester, halide and ether reactants may be used. More than one ester, halide and/or ether may be used.

In the carbonylation process of the present invention the hydrocarbyl halide promoter preferably has the same hydrocarbyl group as the reactant and is most preferably an alkyl halide. The hydrocarbyl halide may be an iodide or bromide and is preferably an iodide. Most preferably the promoter is an alkyl iodide, most preferably methyl iodide. The hydrocarbyl halide is preferably the same as the hydrocarbyl halide used to prepare the catalyst.

The concentration of carboxylic acid anhydride in the liquid reaction composition is preferably in the range 0.1 to 70% by weight, more preferably in the range 5 to 50% by weight.

Carbon monoxide used in the process of the present invention may be essentially pure or may contain inert impurities such as carbon dioxide, methane, nitrogen, noble gases and $C_1$ to $C_4$ paraffinic hydrocarbons. Hydrogen may be present as a co-promoter in the carbon monoxide.

The process of the present invention is suitably performed at a total pressure in the range 1 to 500 barg, preferably 10 to 80 barg.

The process of the present invention is suitably performed at a temperature in the range 50° to 250° C. but the upper operating temperature depends upon the thermal stability of the catalyst. Preferably, the temperature is in the range 100° to 200° C., most preferably in the range 150° to 200° C.

The process of the present invention may be performed as a batch or continuous process, preferably a continuous process.

The invention will now be illustrated by example only by reference to the following experiments.

Preparation of Preformed Catalyst from Reillex Resin 425

Reillex Resin 425 polymer was dried in an oven at 100° C. for 18 hours and stored in a desicator for use.

If required in quaternised form prior to contacting with rhodium, the polymer was stirred in dichloromethane at room temperature with an excess of hydrocarbyl halide such as methyl iodide before removal of the solvent and drying in vacuo. In Examples 1 to 5 and Experiment A the polymer support was loaded with rhodium and quaternised in situ. In Examples 6 and 7 the polymer support was quaternised in situ before being loaded with rhodium also in situ.

Batch Carbonylation Experiments

A 300 ml Hastelloy (Trade Mark) B2 autoclave fitted with a stirrer was used for batch carbonylation experiments. A gas supply to the autoclave was provided from a gas reservoir vessel, feed gas being provided to maintain the autoclave at a constant pressure during the carbonylation reaction and the rate of gas uptake being calculated with an accuracy believed to be 10% from the rate at which the pressure fell in the gas reservoir.

EXAMPLE 1

The autoclave was charged with [{Rh(CO)$_2$Cl}$_2$] (0.4g) dissolved in acetic acid (28.2g), Reillex Resin 425 (22.9g), acetic anhydride to maintain substantially anhydrous conditions (7.5g), methyl acetate reactant (52.5g) and methyl iodide promoter (38.9g).

The autoclave was flushed with hydrogen and pressurized with 3 barg of hydrogen and 1 barg of carbon monoxide. The autoclave contents were then heated to a temperature of 185° C. with stirring. The pressure in the autoclave was then increased to reaction pressure with carbon monoxide. As the carbonylation reaction proceeded, carbon monoxide was fed to the autoclave from the gas reservoir to maintain the autoclave pressure at 70 barg. The rate of carbon monoxide uptake from the gas reservoir was measured every 12 seconds and from this was calculated the rate of carbonylation, expressed as moles of carbon monoxide per kilogram of autoclave charge (including catalyst) per hour (mol/kg/hr). The reaction was continued for 150 minutes. When the reaction had ceased the contents of the autoclave were cooled to room temperature and the gases vented from the autoclave. The vented gases were analyzed and were found to contain 0.1 and 0.5% v/v of carbon dioxide and methane by-products respectively. The contents were allowed to settle and a fraction of the solution was removed, centrifuged and the resulting clear solution analyzed for carboxylic acid anhydride concentration by gas chromatography and for rhodium concentration by atomic absorption spectroscopy.

The methyl acetate concentration in the autoclave was calculated from the carbon monoxide uptake as the reaction progressed. When the methyl acetate concentration was calculated to be 25% by weight, the rate of reaction based on carbon monoxide uptake was 4.7 mol/kg/hr. 633 mmol of carbon monoxide were consumed in the reaction. Analysis of the centrifuged solution at the end of the experiment showed that it contained 58% w/w of acetic anhydride and only trace amounts of rhodium (2 ppm).

EXAMPLE 2

Example 1 was repeated using 0.79g of [{Rh(CO)$_2$Cl}$_2$]. The amount of acetic acid charged to the autoclave was adjusted so that the total mass of charge remained constant at 150g. The reaction was continued for 160 minutes. The rate of reaction was 2.0 mol/kg/hr at 25% by weight methyl acetate concentration.

This Example shows that at least under the reaction conditions employed in Example 1, a decrease in rate of reaction is observed when the amount of rhodium on the support is increased from about 0.4% rhodium (as metal) by weight of the catalyst (Example 1) to about 0.8% rhodium by weight of the catalyst (Example 2).

EXAMPLE 3

Example 1 was repeated at a constant pressure of 40 barg, and a temperature of 185° C. for 2 hours 36 minutes. The rate of reaction was 3.1 mol/kg/hr at 25% by weight methyl acetate concentration. 466 mmol of carbon monoxide were consumed in the reaction. Analysis of the gases vented at the end of the experiment showed that they contained 0.1 and 0.9% v/v of carbon dioxide and methane by-products respectively. Analysis of the centrifuged solution at the end of the experiment showed it to contain 54% w/w of acetic anhydride.

EXAMPLE 4

Example 3 was repeated using 0.098g of [(Rh(CO)$_2$Cl)$_2$]. The reaction was continued for 150 minutes. The rate of reaction was 2.4 mol/kg/hr at 25% by weight methyl acetate concentration. Analysis of the gases vented at the end of the experiment showed that they contained 0.2 and 0.8% v/v of carbon dioxide and methane by-products respectively. Analysis of the centrifuged solution at the end of the experiment (150 minutes) showed it to contain 44% w/w of acetic anhydride.

EXAMPLE 5

Example 1 was repeated at a constant total pressure of 28 barg. The rate of reaction was 1.7 mol/kg/hr at 25% w/w methyl acetate concentration. Analysis of the gases vented at the end of the experiment (150 minutes) showed that they contained 0.2 and 1.1% v/v of carbon dioxide and methane by-products respectively.

EXAMPLE 6

This example shows that the rhodium can be introduced to the polymer support once it has been quaternised by heating to reaction temperature in the presence of methyl iodide. The autoclave was charged with Reillex Resin 425 (22.9), acetic acid (16.2g), acetic anhydride to maintain substantially anhydrous conditions (7.5g), methyl acetate reactant (52.7g) and methyl iodide promoter (38.9g).

The autoclave was flushed with hydrogen and pressurized with 3 barg of hydrogen and 1 barg of carbon monoxide. The autoclave contents were then heated to a temperature of 185° C. with stirring. Carbon monoxide was introduced to the autoclave until a total pressure of 65 barg was reached and then [(Rh(CO)$_2$Cl)$_2$] rhodium compound (0.196 g) dissolved in acetic acid (12.0 g) was injected into the autoclave using an over pressure of carbon monoxide. As the carbonylation reaction proceeded, carbon monoxide was fed to the autoclave from the gas reservoir to maintain the autoclave pressure at 70 barg. The rate of carbon monoxide uptake from the gas reservoir was measured as in Example 1. The reaction was continued for 150 minutes. The methyl acetate concentration was calculated as in Example 1. When the methyl acetate concentration was calculated to be 25% by weight, the rate of reaction based on carbon monoxide uptake was 4.5 mol/Kg/hr. When the methyl acetate concentration was calculated to be 10% by weight, the rate of reaction based on carbon monoxide uptake was 1.4 mol/kg/hr.

The contents of the autoclave were then cooled to room temperature and allowed to settle. The gases were vented from the autoclave and were found to contain 0.3 and 0.6% v/v of carbon dioxide and methane by-products respectively. The reaction composition was allowed to settle and a fraction of the liquid portion of the reaction composition was centrifuged and analyzed for carboxylic acid anhydride and for rhodium concentration.

Analysis of the clear centrifuged solution at the end of the experiment showed that it contained 52% w/w acetic anhydride, 5% w/w methyl acetate (analyzed by gas chromatography) and only trace amounts of rhodium (approximately 5 ppm close to the detection limit of the AA analysis).

The catalyst was recovered by decanting the liquid portion of the reaction composition. Approximately 2g of the recovered catalyst were placed on an evaporating dish and the resin was air dried in a well ventilated fume cupboard at room temperature. Dried resin (0.1g), concentrated sulphuric acid (2 ml) and fuming nitric acid (1 ml) were charged to a pyrex tube which was placed in a metal block. The contents of the pyrex tube were heated to 150°–180° C. and fuming nitric acid (ca. 0.2 ml) was added to the heated solution at hourly intervals. The reaction was continued for 16 hours before the contents of the pyrex tube were cooled to room temperature and analyzed by atomic absorption spectroscopy which showed that the catalyst contained 1930 ppm of rhodium (approximately 0.2% rhodium by weight).

EXAMPLE 7

Example 6 was repeated using 0.05g of [{Rh(CO)$_2$Cl}$_2$]. The amount of acetic acid charged to the autoclave was adjusted so that the total mass of charge remained constant at 150 g. The reaction was continued for 141 minutes. The rate of reaction was 3.0 mol/kg/hr at 25% by weight methyl acetate concentration. The gases vented from the autoclave were found to contain 0.1 and 0.2% v/v of carbon dioxide and methane by-products respectively. Analysis of the clear centrifuged solution at the end of the experiment showed that it contained 42.0% w/w acetic anhydride and 6.4% w/w methyl acetate.

This Example shows that, at least under the reaction conditions employed in Examples 6 and 7, an increase in rate of reaction is observed when the amount of rhodium on the support is increased from about 0.05% rhodium (as metal) by weight of the catalyst (Example 7) to about 0.2% rhodium by weight of the catalyst (Example 6).

High Pressure Infra-red (HPIR) Experiments

EXAMPLE 8

The following experiment was performed to show that rhodium remains bound to the polymer support during a carbonylation reaction under substantially anhydrous conditions with carboxylic anhydride but no water in the reaction composition.

A 50 ml Hastelloy B2 high pressure infra-red fitted with calcium fluoride windows was charged with catalyst comprising rhodium supported on Reillex resin 425 (3.81g) which catalyst had been recovered from a carbonylation reaction as described in Example 1, together with methyl iodide promoter (2.75g), methyl acetate reactant (6.25g), acetic acid solvent (5.52g) and acetic anhydride (2.47g). The cell was flushed with hydrogen and pressurized to 1 bara with hydrogen and then to 20 bara with carbon monoxide. The liquid composition in the cell was heated to 185° C. with stirring and the pressure adjusted to 70 bara. Carbon monoxide was added on demand to maintain the cell at 70 bara. The reaction was allowed to proceed for 90 minutes. Infra-red spectra of the liquid composition were taken throughout the course of the reaction. These indicated that there were no rhodium carbonyl species in the liquid composition indicating that the rhodium species remained predominantly bound in the polymer support during the reaction.

At the end of 90 minutes the cell was cooled to ambient temperature and the contents allowed to settle.

Analysis of the liquid reaction composition at the end of the experiment showed it to contain 5.39g (24.5% by weight) of acetic anhydride.

Experiment A

The following experiment was performed to show that rhodium is present in the reaction composition in the presence of water in an aqueous carbonylation process. The high pressure infra-red cell was charged with catalyst comprising Reillex resin 425 (2.53g) previously quaternised with methyl iodide and loaded with [Rh(CO)$_2$Cl]$_2$ (0.1g Rh on 8.68 g resin) which catalyst had been recovered from a methanol carbonylation reaction in the presence of a finite amount of water. The cell was also charged with methyl iodide (3.70 g), methyl acetate (8.87 g), water (4.42 g) and acetic acid (8.00 g). The cell was then flushed with and pressurized to 20 bara with carbon monoxide. The reaction was performed at a constant pressure of 30 bara and a temperature of 180° C. for 2 hours. Analysis of the liquid reaction composition at the end of the experiment showed it to contain 14.11 g of acetic acid (54.71) % w/w. Infra-red spectra showed an initial high concentration of Rh(CO)$_2$I$_2^-$ in solution (400 ppm). The concentration of this species declined through the course of the reaction until the concentration of Rh(CO)2I$_2^-$ at the end of the reaction was 10–20 ppm.

This is not an experiment according to the present invention because water is present in the reaction composition throughout the course of the experiment.

We claim:

1. A process for the production of a carboxylic acid anhydride which process comprises contacting a reaction composition comprising a carboxylic acid ester, a hydrocarbyl halide and/or a hydrocarbyl ether reactant and a hydrocarbyl halide promoter with carbon monoxide in the presence of a catalyst comprising an insoluble polymer support having pendant quaternised N-base or alkylated N–oxide pyridine groups supporting a rhodium species in which process there is maintained throughout the process a finite concentration of carboxylic acid anhydride in the reaction composition.

2. A process as claimed in claim 1 in which the reaction composition is a liquid.

3. A process as claimed in claim 1 in which the rhodium species on the polymer support is present at 500 ppm to less than about 4% rhodium (as metal) by weight of the catalyst.

4. A process as claimed in claim 1 in which the insoluble polymer support is a porous cross-linked 4- or 2- vinyl pyridine copolymer in the quaternised base or alkylated N-oxide form which is respectively quaternised or alkylated with an alkyl halide.

5. A process as claimed in claim 4 in which the insoluble polymer support is a porous cross-linked copolymer of 4- or 2- vinyl pyridine and divinyl benzene quaternised with an alkyl halide.

6. A process as claimed in claim 5 in which the polymer is quaternised with methyl iodide.

7. A process as claimed in claim 1 in which the carboxylic acid anhydride is maintained in the reaction composition at a concentration in the range 0.1 to 70% by weight.

8. A process as claimed in claim 1 in which the carboxylic acid ester reactant is methyl acetate.

9. A process for the production of acetic anhydride which process comprises contacting a reaction composition comprising methyl acetate reactant and methyl iodide promoter with carbon monoxide in the presence of a catalyst comprising an insoluble polymer support having pendant quaternised N-base or alkylated N-oxide pyridine groups supporting a rhodium species, in which process there is maintained throughout the process a concentration of acetic anhydride of 0.1 to 70% by weight in the reaction composition.

10. A process as claimed in claim 9 in which acetic acid is coproduced by the controlled introduction of water and/or methanol to the reaction composition.

* * * * *

UNITED STATES PATENT AND TRADEMARK OFFICE
CERTIFICATE OF CORRECTION

PATENT NO. : 5,360,929
DATED : November 1, 1994
INVENTOR(S) : DERRICK J. WATSON, BRUCE L. WILLIAMS, JOHN G. SUNLEY and ROBERT J. WATT It is certified that error appears in the above-indentified patent and that said Letters Patent is hereby corrected as shown below:

Col. 1, l. 30, correct the spelling of the word "pyridines."

Col. 2, l. 52, correct the formula of "$Rh_2O_3$"

Signed and Sealed this

Ninth Day of May, 1995

BRUCE LEHMAN

Attest:

Attesting Officer

Commissioner of Patents and Trademarks